(12) United States Patent
Wu

(10) Patent No.: US 8,268,836 B2
(45) Date of Patent: Sep. 18, 2012

(54) COMPOUND USEFUL AS A C-MET INHIBITOR

(75) Inventor: Zhipei Wu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/188,496

(22) Filed: Jul. 22, 2011

(65) Prior Publication Data
US 2012/0028984 A1    Feb. 2, 2012

Related U.S. Application Data

(60) Provisional application No. 61/369,335, filed on Jul. 30, 2010.

(51) Int. Cl.
   *C07D 487/04* (2006.01)
   *A61K 31/519* (2006.01)
   *A61P 35/00* (2006.01)

(52) U.S. Cl. ................... 514/259.31; 544/263

(58) Field of Classification Search .............. 544/263; 514/259.31
See application file for complete search history.

(56) References Cited

U.S. PATENT DOCUMENTS
2009/0124609 A1    5/2009    Albrecht et al.

FOREIGN PATENT DOCUMENTS

| WO | 2008008539 A2 | 1/2008 |
|---|---|---|
| WO | 2008051805 A2 | 5/2008 |
| WO | 2008051808 A2 | 5/2008 |
| WO | 2009056692 A2 | 7/2009 |
| WO | 2009106577 A1 | 9/2009 |

OTHER PUBLICATIONS

Albrecht, B., et al., "Discovery and Optimization of Triazolopyridazines as Potent and Selective Inhibitors of the c-MET Kinase," Journal of Medicinal Chemistry, 51(10):2879-2882 (2008).
Diamond, S., et al., "Species-specific Metabolism of SGX523 by Aldehyde Oxidase and the Toxicological Implications," Drug Metab Dispos. 38(8):1277-85 (2010).
Liu, X., et al., "Developing c-MET pathway inhibitors for cancer therapy: progress and challenges," Trends in Molecular Medicine, 16(1):37-45 (2010).

*Primary Examiner* — Susanna Moore
(74) *Attorney, Agent, or Firm* — Tina M. Tucker

(57) ABSTRACT

The present invention relates to a c-Met inhibitor or a pharmaceutically acceptable salt thereof useful in treating cancer mediated by activity of c-Met receptors.

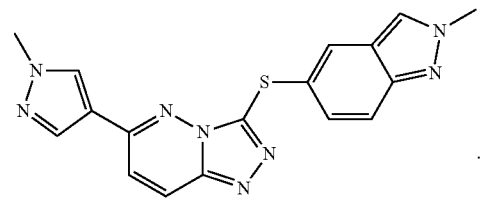

4 Claims, No Drawings

COMPOUND USEFUL AS A C-MET INHIBITOR

This application claims the benefit of U.S. provisional Application No. 61/369,335 filed Jul. 30, 2010.

The present invention is in the field of medicinal chemistry. The invention is related to the treatment of cancer. More specifically, the present invention relates to an inhibitor of the c-Met receptor signaling pathway useful for the treatment of cancer.

c-Met expression occurs in endothelial, epithelial, and mesenchymal cells. Dysregulation of the HGF/c-Met signaling pathway has been implicated in tumor formation and progression. Dys-regulation of tumor cell c-Met receptors enhances tumor cell proliferation, invasion/metastasis, and resistance to apoptosis. (Porter, et al, Small molecule c-Met kinase inhibitors: a review of recent patents, *Expert Opinion on Therapeutic Patents*, (2010), 20(2), 159-177)

Various c-Met receptor inhibitors (c-Met inhibitors) have been reported. For example, Patent Cooperation Treaty (PCT) International publications WO 2008051808 A2, WO 2008/051805 A3, and WO 2009/106577 A1 disclose compounds useful for the treatment of cancer.

Although compounds useful for the treatment of various cancers including inhibitors of c-Met have been reported, some of these compounds are not sufficiently effective. Some compounds lack sustained efficacy, some have unsatisfactory pharmacokinetic/pharmacodynamic (PK/PD), and some have unsatisfactory metabolic profiles. (Xiangdong, et al, *Trends in Molecular Medicine* (2010) 16(1), 41-42; see also: Diamond S, et al, Species-specific metabolism of SGX523 by aldehyde oxidase and the toxicological implications, *Drug Metab Dispos.* 2010, 38(8):1277-85)

Thus, there is a need for novel compounds that are potent and efficacious for the treatment of cancer. In particular, there is a need for compounds that are potent. Additionally, there is a need for compounds that have sustained efficacy. Further, there is a need for compounds that have acceptable PK/PD profile for the treatment of cancer. The present invention provides a novel compound exhibiting high potency, sustained pre-clinical efficacy, and an acceptable PK/PD profile for the treatment of c-Met mediated cancers.

The compound of the invention is a compound of formula

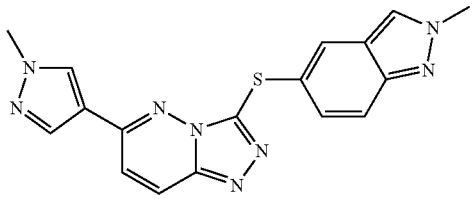

or a pharmaceutically acceptable salt thereof.

The present invention provides a pharmaceutical composition comprising a therapeutically effective amount of the compound of the invention or a pharmaceutically acceptable salt thereof and one or more pharmaceutically acceptable carriers, diluents, or excipients.

The present invention provides a pharmaceutical composition comprising a compound of the invention in combination with one or more pharmaceutically acceptable carriers, diluents, or excipients, and optionally one or more other therapeutic agents.

The present invention provides a method of treating cancer comprising administering a therapeutically effective amount of the compound of the invention or a pharmaceutically acceptable salt thereof, to a patient in need thereof.

The present invention provides a method of treating cancer selected from colorectal, breast, head and neck, prostate, gastric, pancreatic, liver, renal, lung, leukemia, melanomas, glioblastoma and sarcomas comprising administering a therapeutically effective amount of a compound of the invention or a pharmaceutically acceptable salt thereof, to a patient in need thereof.

The present invention relates to a method of treating cancer selected from gastric, glioblastoma, and pancreatic cancer comprising administering a therapeutically effective amount of the compound of the invention or a pharmaceutically acceptable salt thereof, to a patient in need thereof.

The present invention provides a method of treating breast or colorectal cancer comprising administering a therapeutically effective amount of the compound of the invention or a pharmaceutically acceptable salt thereof, to a patient in need thereof.

The present invention provides a compound of the invention or a pharmaceutically acceptable salt thereof for use in therapy.

The present invention provides a compound of the invention for use in the treatment of cancer.

The present invention provides a compound of the invention for use in the treatment of gastric, pancreatic, glioblastoma, breast cancer or colorectal cancer.

The present invention relates to the use of a compound of the invention or a pharmaceutically acceptable salt thereof in the manufacture of a medicament for treating cancer.

The present invention relates to the use of a compound of the invention or a pharmaceutically acceptable salt thereof, in the manufacture of a medicament for treating cancer selected from gastric cancer, pancreatic cancer and glioblastoma.

As used herein 'Met", "c-Met", 'cMet" or "c-Met receptor" refers to the hepatocyte growth factor (HGF) receptor and forms thereof.

The phrase "dysregulation of the HGF/c-Met signaling pathway" means elevated or inappropriate levels of signaling through the HGF/c-Met signaling pathway.

A "therapeutically effective amount" of the compound of the invention is an amount of said compound able to achieve inhibition of c-Met receptor activity in one or more doses to achieve treatment of cancer. An effective amount can be readily determined by the attending physician or diagnostician, as one skilled in the art, by considering a number of factors known to a person skilled in the art such as, for example, size, age, general health of the patient, specific cancer or co-presenting disease(s) being treated, degree of severity, mode of administration, dose regimen, use of concomitant medications, etc.

The terms "treatment" or "treating" as used herein mean tumor growth arrest, inhibition of tumor growth, prevention of occurrence or recurrence of tumor growth, and/or reduction in severity or effect of cancer.

The phrase "sustained efficacy" as used herein refers to a sustained level of pharmacodynamic effect e.g. inhibition of tumor growth, or plasma concentration of the compound of the invention for more than four (4) hours. The benefit of a sustained efficacy includes less frequency and/or amount of dosing.

The phrase "acceptable PK/PD properties" as used herein refers to a profile of pharmacokinetic (PK) and pharmacodynamic (PD) properties that allow the compound to be administered once a day (QD) or twice a day (BID) for the intended purpose i.e. as a treatment of cancer. The PK/PD properties contemplated include parameters such as bioavailability, clearance, and metabolic stability.

The compound of the invention may also exist as an acid addition salt. Pharmaceutically acceptable salts and common methodology for preparing them are known to one of skill in the art. See, e.g. P. Stahl, et al. Handbook of Pharmaceutical Salts: Properties, Selections and Use (VCHA/Wiley-VCH, 200); S. M. Berge, et al., "Pharmaceutical Salts" Journal of Pharmaceutical Sciences, Vol. 66, No. 1, January 1977. Preferred salts of the compound of the invention include the hydrochloric acid salt, methanesulfonic acid salt and the bisulfate salt. One of skill in the art is aware of procedures to make acid salts, particularly, the preferred acid salts of the present invention.

Preferably, the present invention provides a method for the treatment of breast colorectal, breast, head and neck, prostate, gastric, pancreatic, liver, renal, lung, melanomas, sarcomas, leukemia or advanced metastatic cancer. More preferably, the present invention provides a method of treating cancer selected from the group consisting of breast cancer, colorectal, gastric, pancreatic, and advanced metastatic cancer. Also preferred is an embodiment of the present invention comprising administering a therapeutically effective amount of the compound of the invention for the treatment of breast cancer or colorectal cancer. In a most preferred embodiment, the present invention provides a method of treating gastric or pancreatic cancer comprising administering a therapeutically effective amount of a compound of the invention, or a pharmaceutically acceptable salt thereof, to a patient in need thereof.

In a preferred embodiment, the present invention also provides pharmaceutical compositions comprising a compound of the invention in combination with one or more pharmaceutically acceptable carriers, diluents, or excipients. In a particular embodiment the composition further comprises one or more other therapeutic agents.

The compound of the invention may be prepared essentially as described in the examples below.

| Abbreviations | |
|---|---|
| DCM | Dichloromethane |
| DMF | N,N-dimethylformamide |
| EtOAc | Ethyl acetate |
| THF | Tetrahydrofuran |
| DMSO | Dimethylsulfoxide |
| RT | Room temperature |
| ACN | Acetonitrile |
| IPA | Isopropyl alcohol |

Preparation 1

3-Chloro-6-(1-methyl-1H-pyrazol-4-yl)pyridazine

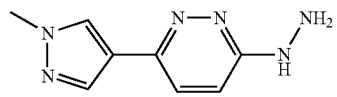

To a 3000 mL round bottom flask containing a solution of 1-methyl-(4,4,5,5-tetramethyl-1,3,2-dioxaborolan-2-yl)-1H-pyrazole (76 g, 365.3 mmol), 3,6-dichloropyridazine (68 g, 456.4 mmol) in 1,4-dioxane (1200 mL) is added a aqueous solution of $K_2CO_3$ (127 g, 919 mmol) in water (480 mL). After [1,1'-bis(diphenylphosphino)ferrocene]palladium(II) chloride (7.5 g, 9.2 mmol) is added, the mixture is purged with $N_2$ for 20 min and stirred at 80° C. for 16 h. The reaction mixture is poured into water (300 mL) and dichloromethane (2000 mL), and the aqueous layer is extracted with DCM (3×800 mL). The combined organic layers are dried over anhydrous $Na_2SO_4$ and concentrated under vacuum. The crude product is purified with silica gel column eluting with DCM/methanol (40:1) to give the title compound as a pale yellow solid (56 g, 63.1%). MS (m/z): 195.1 (M+H).

Preparation 2

3-Hydrazinyl-6-(1-methyl-1H-pyrazol-4-yl)pyridazine

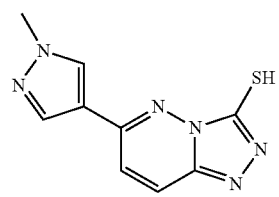

To a 1000 mL round bottom flask containing a solution of hydrazine monohydrate (280 mL, 4.89 mol) in ethanol (300 mL) is added 3-chloro-6-(1-methyl-1H-pyrazol-4-yl)pyridazine (60 g, 308.3 mmol) at 4° C. The resulting clear solution is heated to reflux for 18 h, and then cooled to 10° C. The product precipitated is collected by filtration and dried under vacuum to give the title compound as a white solid (53 g, 90.4%) and is used as is.

Preparation 3

6-(1-Methyl-1H-pyrazol-4-yl)-[1,2,4]triazolo[4,3-b]pyridazine-3-thiol

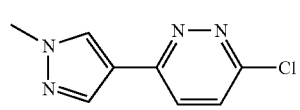

To a solution of 3-hydrazinyl-6-(1-methyl-1H-pyrazol-4-yl)pyridazine (53 g, 278.6 mmol) in ethanol (550 ml) is added an aqueous solution of KOH (17.2 g, 306.6 mmol) in water (130 mL), followed by $CS_2$ (36 mL, 596.7 mmol). The mixture is stirred at 60-67° C. for 3 h under $N_2$ atmosphere and cooled to RT. Solvents are removed under vacuum and the residue is dissolved in 1N aqueous NaOH (350 mL). The insolubles are filtered off and the filtrate is acidified to pH 2-3 with 1N aqueous HCl. The precipitate is collected, washed with water, and dried under vacuum to provide the title compound (50 g, 77.3%). MS (m/z): 233.0 (M+H).

Preparation 4

1H-indazol-5-amine

To a 5000 mL autolcave equipped with a $H_2$ inlet, a thermometer, and a mechanical stirrer is added a solution of 5-nitro-1H-indazole (500 g, 3.06 mol) in tetrahydrofuran (THF, 3500 mL), followed by palladium on carbon (10%, 50 g, 141 mmol). The resulting mixture is stirred overnight at 25° C. under H$_2$ atmosphere (5 kg pressure). After it is purged with N$_2$, the mixture is filtered, and the filtrate is concentrated under vacuum to give the title compound (420 g, 100%) as a brown solid. MS (m/z): 134.1 (M+H).

Preparation 5

5-iodo-1H-indazole

To a solution of concentrated HCl (1.3 L, 15.8 mol) in water (3.5 L) is added 1H-indazol-5-amine (500 g, 3.8 mol), followed by a solution of NaNO$_2$ (285 g, 4.1 mol) in water (1 L) in portions at 0-5° C. The resulting red suspension is added slowly to a solution of KI (3.1 kg, 18.7 mol) in water (3 L) at 50° C. to keep gas generation in control. The resulting mixture is stirred at 50° C. for 1.5 h, cooled to 10° C. and basified to pH 8 with saturated aqueous Na$_2$CO$_3$ solution. The solids are collected by filtration and redissolved in ETOAc (20 L). The solution is washed with saturated aqueous Na$_2$SO$_3$ solution (3×5 L), dried over anhydrous Na$_2$SO$_4$ and filter through a short silica gel column. The filtrate is concentrated under vacuum to provide the title compound (680 g, 74.2%). MS (m/z): 244.9 (M+H).

Preparation 6

5-iodo-2-methyl-2H-indazole

To a solution of 5-iodo-1H-indazole (500 g, 2.05 mol) in EtOAc (4 L) is added trimethyloxonium tetrafluoroborate (450 g, 3.04 mol). After the resulting white suspension is stirred at room temperature for 2 h, it is concentrated under vacuum. Ice water (1 L) is added to the residue, and it is basified to pH 12 with 10% aqueous NaOH solution. The solids are collected by filtration, and redissolved in DCM (5 L). The insolubles are filtered off and the filtrate is washed with 10% aqueous NaOH solution (2×100 mL). The organic layer is dried over anhydrous Na$_2$SO$_4$, filtered through a short silica gel column, and concentrated. Methyl tert-butyl ether is added to the residue to give a slurry and the product is collected by filtration to give the title compound (360 g, 68.0%). MS (m/z): 259.0 (M+H).

EXAMPLE 1

6-(1-Methyl-1H-pyrazol-4-yl)-3-(2-methyl-2H-indazol-5-ylthio)-[1,2,4]triazolo[4,3-b]pyridazine

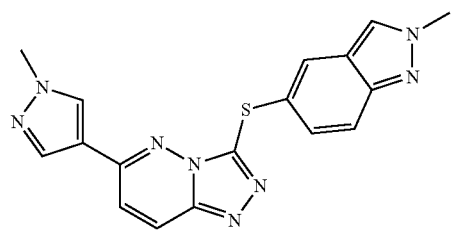

To a solution of 6-(1-methyl-1H-pyrazol-4-yl)-[1,2,4]triazolo[4,3-b]pyridazine-3-thiol (2.3 g, 10.0 mmol) in DMF (20 mL) is added 5-iodo-2-methyl-2H-indazole (2.6 g, 10.0 mmol), tris(dibenzylideneacetone) dipalladium(0) (460 mg; 502.7 μmol), 4,5-bis(diphenylphosphino)-9,9-dimethylxanthene (580 mg, 1.0 mmol), diisopropylethylamine (4 mL, 22.9 mmol). The mixture is purged with N$_2$ and stirred at 100° C. for 18 h. DMF is removed under vacuum, and the residue is purified by flash column chromatography (Combi-Flash, silica gel) eluting with DCM/methanol (20:1) to give a crude product. The crude product is suspended in 20 mL of DCM to give slurry, and the pure product is collected by filtration to afford the title compound (1.9 g, 52.5%) as a yellow solid. MS (m/z): 363.1 (M+H).

EXAMPLE 1A 6-(1-Methyl-1H-pyrazol-4-yl)-3-(2-methyl-2H-indazol-5-ylthio)-[1,2,4]triazolo[4,3-b]pyridazine

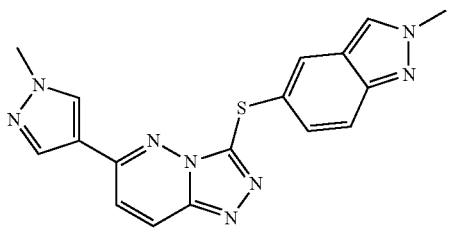

To a solution of 6-(1-methyl-1H-pyrazol-4-yl)-[1,2,4]triazolo[4,3-b]pyridazine-3-thiol (50 g, 268 mmol) in DMF (750 mL) is added 5-iodo-2-methyl-2H-indazole (55.5 g, 215.1 mmol), 2-Pyridinecarboxylic Acid (5.5 g, 44.7 mmoles), Copper (I) Iodide (4 g, 21.0 mmoles), and Cesium Carbonate (212.5 g, 652.2 moles). The mixture is under N$_2$ and stirred at 100° C. for 10 hours. The reaction mixture is then cooled to room temperature and poured into water (2000 mL). After stirring at room temperature for 30 min, the mixture is extracted with a mixed solvent (2 L×2, CHCl$_3$/IPA=3/1). The combined organic layer is then washed four times with mixed solution (25% NH$_4$OH$_{(aq)}$/brine=¼; 800 mL), sat. LiCl$_{(aq)}$ (1 L), sat. brine (1.5 L×2), and dry over Na$_2$SO$_4$. The organic solution is concentrated under reduced pressure to give a brown crude solid product. The crude product is triturated with ethyl acetate (800 mL) at room temperature for 3 hours and the pure product is collected by filtration to afford the title compound (68 g, 87.2%) as a white solid. MS (m/z): 363.0 (M+H).

The compound of the present invention has been observed to be of high potency, to be of high selectivity for the c-Met receptor, to exhibit acceptable PK/PD properties, and to and demonstrate sustained efficacy.

The following assays performed essentially as described herein demonstrate that the compound of the present invention potently inhibits c-Met phosphorylation in cells, potently inhibits c-Met in vivo, and demonstrates dose dependent anti-tumor activity in certain xenograft models.

cMet Homogeneous Time Resolved Fluorescence (HTRF) In Vitro Assay

This assay is based on HTRF technology and it is used to detect the phosphorylation of biotin labeled tyrosine peptide by cMet enzyme. After the reaction is completed, XL665 labeled streptavidin is used to recognize the biotin unit and a Europium (Eu3+) labeled anti-phospho-tyrosine antibody is used to recognize the phosphorylated tyrosine. The detection process relies on the transfer of energy between the excited Eu3+ and the XL665 labeled streptavidin. The aim of this protocol is to calculate the ability of test compounds to inhibit the phosphorylation of the product of this reaction and calculate their relative $IC_{50}$ values.

A reference compound, if desired, may be prepared as a 1 mM stock solution in 100% DMSO and test compounds are prepared as 10 mM stock solutions in 100% DMSO. 1 mM reference compound and 10 mM test compounds are pre-diluted to 8 µM and 80 µM 10% DMSO solutions in a 96-well dilution plate. Compounds are serially diluted (1:3) using Tecan Freedom EVO 200 and 10-point dilution curves are generated for each of the compounds tested. 10 µL of serially diluted compounds are transferred to a 96-well assay plate using Temo (Tecan). Each assay plate contains enzyme maximum activity and enzyme minimum activity controls. Maximum activity control wells contain 10 µL of 10% DMSO and minimum activity control wells contain 10 µL 500 mM ethylene diamine tetraacetic acid (EDTA) dissolved in 10% DMSO. 20 µL of substrate solution [Bio-PolyGT (CisBio) (0.576 µM) and ATP (65.14 uM) prepared in enzyme dilution buffer (EDB) Tris (hydroxymethyl) aminomethane, Trizma® base buffer, pH 7.5, 50 mM; DL-dithiothreitol (DTT), 2 mM; 0.0005% TX-100; $MgCl_2$, 10 mM; and EDTA, 250 µM)] is added to the assay plate using Multidrop (Thermo). 10 µL of enzyme mixture [cMET (12 nM) prepared in EDB] are added to the assay plate using Multidrop (Thermo) to initiate the reaction. The assay plate is shaken for 30 sec and then incubated at RT for 90 min. Following the 90 min incubation, 40 µL of detection buffer are added to the assay plate [Streptavidin-XL665 (SA-XL665) (Cisbio) (144 nM) and Eu3+ labeled anti-phospho tyrosine antibody (EuK) (CisBio) (6 nM) prepared in 2.6*KF/EDTA 4-(2-Hydroxyethyl)piperazine-1-ethanesulfonic acid; N-(2-Hydroxyethyl)piperazine-N'-(2-ethanesulfonic acid (HEPES) buffer, pH 7.0, 50 mM; BSA, 0.2%; EDTA, 20 mM; KF, 800 mM)] using Multidrop (Thermo). The assay plate is incubated at RT for 60 min before reading the fluorescence signals at 620 nm emission and 665 nm excitation in a Victor3 instrument (PerkinElmer Corporation). The 665/620 ratios are normalized for each plate and the percent inhibition values are plotted against compound concentration to calculate the relative $IC_{50}$ values. The $IC_{50}$ value for the compound of example 1 is 0.010 µM with a standard deviation of 0.00071 and a sample size of 2. The $IC_{50}$ value for the mesyalte salt form of example 1 is 0.025 µM with a standard deviation of 0.0082 and a sample size of 2. These data demonstrate that the compound of the invention is a potent inhibitor of c-Met.

HGF Stimulated Met (pY1349) NCl—H460 Cell-based ELISA

NCl—H460 cells (purchased from ATCC) are cultured in RPMI 1640 media (Invitrogen) supplemented with 10% Fetal Bovine Serum (FBS) and plated (prior to becoming 70% confluent) in 96-well flat-bottom plates at a density of 20,000 cells per well in 80 µL volume. The cells are then incubated overnight in a cell culture incubator (5% $CO_2$, 95% Relative Humidity (RH) and 37° C.) and allowed to attach to the plate. The following morning the cells are washed with 2 volumes of a Reduced Serum Media (RSM, RPMI 1640 media supplemented with 0.5% FBS). After removal of the last wash, 80 µL of RSM is added to each well of the cell plates. The cell plates are incubated for 2.5 h in a cell culture incubator, and then dosed with compounds. Compound inhibitors are first solubilized at 10 mM in 100% DMSO and then diluted to 100 µM with 2% DMSO RSM. Subsequently compound serial dilutions (1:3) are prepared over a 100 µM to 0.005 µM range. Cells are dosed with the addition of 20 µL of compound stock to produce a final DMSO concentration of 0.4% and a final compound concentration dose range between 20 and 0.001 µM. After dosing with compounds the cell plates are gently agitated to mix and then allowed to incubate for 30 min in a cell culture incubator. After dose completion, the cells are stimulated with the addition of 20 µL per well of Hepatocyte Growth Factor (HGF) at a final concentration of 100 ng/mL in RSM (all wells except MIN wells are stimulated, MIN wells are dosed with 20 µL RSM). After 10 min incubation in a cell culture incubator, the liquid is removed from the cell plate wells, and the cells are lysed by the addition of 50 µL of ice-cold Meso Scale Discovery® (MSD, Gaithersburg, Md.) 1× Lysis Buffer (150 mM NaCl, 20 mM Tris, pH 7.5, 1 mM EDTA, 1 mM ethylene glycol tetraacetic acid, and 1% TRITON® X-100) supplemented with Phosphatase I and II and Protease inhibitors (Sigma, St. Louis, Mo.). After lysis at RT for 30 min the lysates are transferred to and captured on a MSD® Multi-Spot 96-well 4-spot PhosphoMet plate that is BSA-blocked (at 30 mg/mL Block A in 1× Tris Wash Buffer) and then washed one time with Tris Wash Buffer. After 2 h capture (at RT) the lysates are removed from the MSD® plate and the plate is washed with 1× Tris Wash Buffer. After blotting, 25 µL of 5 nM Sulfo-Tag Anti-Total Met antibody (detection antibody, MSD® prepared in 1× Tris Wash Buffer supplemented with 10 mg/mL BSA and 0.1% Blocker D-R (MSD®)) is added to the wells of the MSD® plate. After 1 h capture (at RT) the MSD® plate wells are washed with 1× Tris Wash Buffer, and then 150 µL of 1× Read Buffer T (with surfactant, MSD®) is added. Immediately after the addition of the Read Buffer, the plates are analyzed with a SECTOR 6000 MSD® Imager plate reader. Relative $IC_{50}$ values are determined using MSD activity units by calculating percent inhibition with respect to on-plate "MIN" and "MAX" controls and then fitting the percent inhibition values and ten-point dose response data to a four-parameter logistic equation. The compound of example 1 showed a relative $IC_{50}$ value of 0.036 µM, n=1 (0.038 µM, n=1 for the mesylate salt form) indicating the compound of example I potently inhibits c-Met phosphorylation in cells in vitro.

c-Met in Vivo Target Inhibition (IVTI) Assay

S114 cells (over-expressing both human HGF and human c-Met) are cultured in a growth media (Dulbecco's Modified Eagle Medium) supplemented with 10% fetal calf serum and expanded. Cells are harvested and washed twice with phosphate buffered saline and 2×10[6] cells are mixed with equal volume of BD Matrigel™ matrix (BD Bioscience, Franklin, N.J.), and injected subcutaneously into the flank of nude mice (athymic nude, from Harlan, Indianapolis, Ind.). At day 8 after implant, compounds (formulated in 10% acacia or 1% carboxymethylcellulose/0.5% sodium lauryl sulfate/0.05% antifoam as suspension) are administered to animals by oral gavage at 50 mg/kg. Animals are sacrificed at 2 h post dose, and tumors are harvested and stored frozen until needed.

Frozen tumors are pulverized using motar-pestel. The pulverized tissues are transferred to a tube containing Lysing Matrix D beads (MP Biomedicals, Solon, Ohio) and 600 µL lysis buffer (RIPA buffer, containing 50 mM Tris-HCl, pH 7.4, 150 mM NaCl, 1% NP-40, 0.5% sodium deoxycholate, 0.1% SDS, from Boston Bioproducts, Phosphatase Inhibitors I and II and Protease Inhibitor (Sigma, St. Louis, Mo.)). A FastPrep® Cell Disrupter (MP Biomedicals, Inc.) is used to disrupt the tissue and lyse the cells. Lysates are passed through a 20 gauge needle and transferred to a clean tube. Protein concentration is determined by Bradford method known to one of skill in the art.

Tumor lysates are loaded onto MSD® phosphor-Met ELISA plates and phosphor-c-Met level is determined using the same protocol as H460 cell-based ELISA. The S114 in vivo inhibition $ED_{50}$ value for the compound of example 1 is 0.32 mg/kg with a 95% confidence interval bounded by 0.23 mg/kg and 0.41 mg/kg. The $TEC_{50}$ for example 1 is 0.18 µM with a 95% confidence interval bounded by 0.13 µM and 0.23 µM. These results indicate that example 1 is a potent c-Met inhibitor in vivo.

Xenograft Tumor Models

Human glioblastoma cells U87MG, human gastric cancer cells MKN45, or human pancreatic KP4 cells are cultured and implanted subcutaneously in the rear flank of female CD-1 nu/nu strain mice which have been acclimated for one week in the animal facility after receipt from the vendor. Mice are randomized into groups of 10 mice per group. Testing compound is prepared in an appropriate vehicle and is administered by oral gavage when tumors are established (7-21 days after implant, or when the mean tumor volume reaches ~100 mm$^3$). Tumor response is determined by tumor volume measurement performed twice a week during the course of treatment. Fluctuations in body weight are also monitored as a general measurement of toxicity. The compound of example 1 is orally administered twice a day for 28 days.

For statistical analysis, the individual subject tumor volumes are transformed to log volume and are analyzed with a two-way repeated measures analysis of variance by time and treatment using the MIXED procedures in SAS software (version 8.2). The correlation model for the repeated measures is spatial power. Treated groups are compared to the control group at the final time point. The MIXED procedure is also used separately for each treatment group to calculate adjusted means and standard errors at each time point. Both analyses account for the autocorrelation within each subject.

TABLE 1

Antitumor efficacy of Example 1 in U87MG glioblastoma xenografts

| Treatment Group | Mean Tumor Volume ± Standard Error (mm$^3$) | p-value at day 37 |
|---|---|---|
| Vehicle | 479 ± 175 | — |
| Example 1 at 2 mg/kg | 271 ± 61 | Not Significant |
| Example 1 at 4 mg/kg | 137 ± 29 | <0.001 |
| Example 1 at 8 mg/kg | 108 ± 16 | <0.001 |
| Example 1 at 16 mg/kg | 116 ± 19 | <0.001 |
| Example 1 at 32 mg/kg | 46 ± 4 | <0.001 |

TABLE 2

Antitumor efficacy of Example 1 in MKN45 gastric xenografts

| Treatment Group | Mean Tumor Volume ± Standard Error (mm$^3$) | p-value at day 37 |
|---|---|---|
| Vehicle | 736 ± 115 | — |
| Example 1 at 4 mg/kg | 329 ± 54 | <0.001 |
| Example 1 at 8 mg/kg | 296 ± 29 | <0.001 |
| Example 1 at 16 mg/kg | 166 ± 10 | <0.001 |
| Example 1 at 32 mg/kg | 161 ± 14 | <0.001 |

TABLE 3

Antitumor efficacy of Example 1 in KP4 pancreatic xenografts

| Treatment Group | Mean Tumor Volume ± Standard Error (mm$^3$) | p-value at day 37 |
|---|---|---|
| Vehicle | 1123 ± 125 | — |
| Example 1 at 2 mg/kg | 1229 ± 83 | Not Significant |
| Example 1 at 4 mg/kg | 1085 ± 256 | Not Significant |
| Example 1 at 8 mg/kg | 627 ± 74 | <0.01 |

TABLE 3-continued

Antitumor efficacy of Example 1 in KP4 pancreatic xenografts

| Treatment Group | Mean Tumor Volume ± Standard Error (mm$^3$) | p-value at day 37 |
|---|---|---|
| Example 1 at 16 mg/kg | 554 ± 47 | <0.001 |
| Example 1 at 32 mg/kg | 273 ± 42 | <0.001 |

These data demonstrate that the compound of the invention inhibits tumor growth in vivo.

The compound of the invention has been found to exhibit superior in vivo properties relative to structurally related compounds, such as example 25 of WO 2008051808 A2 hereinafter "the reference compound." The reference compound and the compound of the invention have similar molecular weights and comparable in-vitro potency which are within the minimum significant ratio (MSR) thus not statistically different (c-Met IC$_{50}$ of 0.010 µM for compound of example 1 compared to 0.015 µM for the reference compound). The H460 assay showed an IC$_{50}$ of 0.036 µM for the compound of example 1 compared to 0.065 µM for the reference compound. For the H460 assay the potency values are within the MSR and are not statistically different from each other.

Similarly, both the compound of example 1 and the reference compound are highly selective for the c-Met receptor. In a Cerep screening of 99 kinases employing the Express Diversity Kinase Profile™, both compounds inhibited only c-Met. The Express Diversity Kinase Profile™ is a screening service developed by Cerep SA (Paris, France). Details of assay conditions and/or contact information can be found on their website http://www.cerep.fecerep/users/pages/catalog/profiles/catalog.asp).

However, head to head comparison of the compound of example I against the reference compound show that after 8 hours the compound of formula I exhibits a significant advantage in plasma exposure and phospho cMET inhibition in S114 tumors compared to the reference compound in in vivo tumor inhibition studies as shown in the table 4 below.

TABLE 4

| Test | Compound of Example 1 | Reference Compound | p-value |
|---|---|---|---|
| Plasma conc. (ng/mL) 8 mg/Kg after 8 h | 141 | 14 | <0.0001 |
| Plasma conc. (ng/mL) 20 mg/Kg after 8 h | 318 | 17 | <0.0001 |
| % phos-Met inhibition at 8 mg/kg after 8 h | 75 | −5.45 | <0.0001 |
| % phos-Met inhibition at 20 mg/kg after 8 h | 93 | 0.57 | <0.0001 |
| Single dose IVTI % inhibition after 2 h** | 98*** | 84**** | |

**performed in experiments separate from head to head study
***16 mg/Kg dose administered
****20 mg/Kg dose administered The above results indicate that the compound of example 1 produces a more sustained pharmacodynamic effect (over 8 hours) compared to the reference compound. The above data suggests that the compound of example 1 may be dosed less frequently (e.g. BID or daily regimen) while the reference compound may require much more frequent dosing regimens that may engender compliance issues by the caregiver or the patient. Analysis of the % phos-Met inhibition data show that the plasma concentration for both doses (8 mg/kg and 20 mg/kg) of the compound of example 1 are statistically different compared to corresponding doses of the reference compound with a p-value of <0.0001. Further, both doses of the compound of example 1 are statistically different from the vehicle group, p<0.0001, and also statistically different from each other, p=0.0058. These data were analyzed using one-way analysis of variance. The experimentwise error rate for all pairwise comparisons was strictly controlled at 5% using Tukey's method for multiple testing.

In IVTI studies, each compound is administered orally and formulated in 10% w/v acacia. Mouse blood samples are collected with anti-coagulant (EDTA-purple top Vacutainer tube) post-dose using cardiac puncture techniques. Tubes are inverted for 3-5 times and are placed on ice until centrifugation at 3000 RPM (1800×g) for 10 min at 4° C. to obtain plasma. Aliquots of plasma are pipetted and stored in a clean 96 well plate. Plasma samples are stored immediately at −80° C. Shipments of plasma samples are packed in dry ice and samples are frozen at −80° C. until analysis.

A 0.1-mg/mL stock solution of each drug was prepared and is serially diluted into pooled mouse plasma to prepare standards ranging from 1 to 5000 ng/mL. Plasma standards or samples (0.025 mL) in 96-well plates are treated by protein precipitation with the addition of a 0.1-0.2 ml of methanol: acetonitrile (1/1, v/v) containing internal standard. The mixtures are centrifuged at 4000 rpm at 4° C. for 10 min and aliquots (0.05 mL) of the resulting supernatant fractions are transferred to a different 96-well plate. Samples and standards are analyzed with a Sciex API 4000 Triple Quadrupole Mass Spectrometer (Sciex, Division of MDS Inc., Toronto, Canada) coupled to a Shimadzu HPLC System (LC-10AD, Shimadzu Corporation) and a Gilson 215 Autosampler. Samples (0.01 mL) are injected onto a HPLC column of 5-μm Betasil C18 20×2.1 mm Javelin (Thermo Electron Corp. Cat#70105-022106) and eluted with a gradient. The chromatographic conditions consisted of mobile phase A of water/ 1M $NH_4HCO_3$ (2000:10, v/v) and mobile phase B of MeOH/ 1M N $NH_4HCO_3$ (2000:10, v/v) that is run over a 2.5-min gradient at a flow rate of 1.5 mL/min. A positive ion mode with turbo spray and an ion source temperature of 740° C. are utilized for mass spectrometric detection. Quantitation is performed using multiple reaction monitoring (MRM) at the following transitions: Example 1 (m/z 363.05 to m/z 163.10) and the reference compound 20 (m/z 363.05 to m/z 163.10). Linear regression plots of compounds to internal standard peak area ratios versus drug concentrations are derived with $1/x^2$ Quadratic.

The compound of the present invention is also significantly more soluble than the reference compound.

The solubility of Example 1 and the reference compound (example 25 of the '808 publication) are measured by placing a small quantity of each in a glass vial, capping and rotating the vial overnight at ambient conditions (18 h). The media included simulated gastric fluid (SGF) which comprise of 0.01N HCl, 0.05% sodium lauryl sulfate, and 0.2% NaCl; fasted state simulated intestinal fluid (SIF-fasted) which composed of 29 mM $NaH_2PO_4$, 3 mM Na taurocholate, 0.75 mM lecithin, 103 mM NaCl, and NaOH to pH 6.5; fed state simulated intestinal fluid (SIF-fed) which comprise of 144 mM acetic acid, 15 mM Na taurocholate, 3.75 mM lecithin, 204 mM NaCl, and NaOH to pH 5.0; and pH 4.5, 6, 7.5 buffers which are 28-56 mM phosphate buffers. The compound concentrations are determined using Agilent 1200 HPLC (LC5) with a UV detector. Mobile phase uses A (85%) which is water containing 0.1% TFA and B (15%) which is ACN at a flow rate of 1 mL/min and run time of 10 min. Column of Zorbax, Bonus-RP (3.5 μm, 4.6×75 mm; SN: USTM002428) is used in the studies.

The data below shows that the compound of Example 1 is approximately 13 and 14-fold more soluble in the simulated intestinal fluid (SIF) at fasted and fed states respectively when compared to the reference compound.

TABLE 5

| | Dynamic solubility mg/mL | |
|---|---|---|
| Test | Compound of Example 1 | Reference compound |
| SGF | 0.052 | 0.057 |
| SIF Fasted | 0.013 | 0.001 |
| SIF Fed | 0.070 | 0.005 |
| 0.1N HCl | 0.033 | 1.894 |
| 0.01N HCl | 0.011 | 0.332 |
| Water | 0.009 | 0.001 |
| pH ≧ 4 buffer | ~0.010 | ~0.002 |

Solubility 2: Kinetic Solubility Screens

The assay is used to determine the concentration range in which a compound that has been pre-solubilized in DMSO at 10 mM will precipitate from a solution. The assay is conducted in a screening format on a 96-well plate and measures the nephelometry (light scattering) from precipitated compound in aqueous phosphate buffer (50 mM; pH 7.4). This method consists of a 2-hour RT (room temperature) incubation of compound in buffer at concentrations of 10, 20, 40, 60, 80, and 100 μM (where % DMSO is kept constant). Plates are pre-read by the nephelometer to determine if scratches or dust particles are present and this is used for background subtraction. The reported values are the concentrations at which the last soluble and first insoluble are achieved. These assays are not optimized to assess equilibrium solubility or determine a "true" kinetic solubility.

The screening data below shows that the compound of Example 1 is at least 3-fold more soluble in pH 7.4 buffer when compared to the reference compound.

TABLE 6

| Test compound | $1^{st}$ insoluble pH 7.4 | Last soluble pH 7.4 |
|---|---|---|
| Example 1 (μM) | Non detect | >100 |
| Reference (μM) | 49 | 29 |

The compound of the invention shows a significant difference in pharmacokinetic parameters compared to the reference compound in rat bioavailability studies. The compound of the present invention provides a 18-fold lower plasma clearance and 4-fold longer terminal elimination half life following a 1 mg/kg intravenous dose in solution formulation. Following a 10 mg/kg oral dose in 10% acacia suspension formulation, the compound of the present invention provides a 57-fold and 93-fold higher exposure measured by peak plasma concentration or plasma area under the curve (AUC), respectively. The oral bioavailability of the compound of the present invention is 65.8% compared to 14.6% for the reference compound, a 4.5-fold increase.

In rat bioavailability studies, each compound is administered intravenously (IV) or orally (PO). Intravenous dosing is formulated in solution formulation and oral dosing is formulated in 10% w/v acacia. Rat blood samples are collected using anti-coagulant (EDTA) collection tubes and centrifugation is performed to obtain plasma samples. Aliquots of plasma are pipetted and stored immediately at <−20° C. Shipments of plasma samples are packed in dry ice if needed and samples are frozen at <−20° C. until analysis.

A stock solution of each drug is prepared and is diluted into pooled rat plasma to prepare standards. Plasma standards or samples are treated by protein precipitation or liquid-liquid extraction using organic solvent containing internal standard. The mixtures are centrifuged and aliquots of the resulting supernatant fractions are transferred. In the case of protein precipitation, supernatant is diluted and analyzed using a Mass Spectrometer coupled to a HPLC System and an autosampler. In the case of liquid-liquid-extraction, supernatant is dried under $N_2$ at 40° C., reconstituted and analyzed using a Mass Spectrometer coupled to a HPLC System and an autosampler. Quantitation is performed using multiple reaction monitoring (MRM) and linear regression plots of compounds to internal standard peak area ratios versus drug concentrations.

TABLE 7

| Test Rat bioavailability | Compound of Example 1* | Reference Compound | p-value |
|---|---|---|---|
| IV Dose (mg/kg) | 1 | 1 | |
| T½ (hrs) | 2.3 | 0.6 | p = 0.0027 (log T½) |
| Cl (ml/min/kg) | 1.7 | 31 | p = 0.0003 |
| Vdss (L/kg) | 0.3 | 0.8 | p = 0.0001 |
| PO Dose (mg/kg) | 10 | 10 | |
| Cmax (ng/ml) | 9401 | 164 | p = 0.0006 (log Cmax) |
| Tmax (hrs) | 3.33 | 0.917 | p = 0.0486 |
| AUC (ng*hr/ml) | 73753 | 794 | p = 0.0002 (log AUC) |
| F % | 65.8 | 14.6 | p = 0.0002 |

*Rat bioavailability performed using mesylate salt of the compound of example 1.

The above data shows that the mesylate salt of compound of example 1 is more bioavailable than the reference compound. Furthermore, for oral dosing purposes, available data suggests similar exposure levels for the base and salt forms of the compound of example 1.

The compound of example 1 may also be formulated and/or administered in a combination regimen with a suitable anticancer agent(s) or other adjuvant therapies. Such combinations may be in the form of a cocktail where individual doses of different therapies are administered together, sequentially or after appropriate intervals.

The compound of the present invention is preferably formulated as a pharmaceutical composition administered by a variety of routes including but not limited to oral, rectal, transdermal, subcutaneous, intravenous, intramuscular, and intranasal. The compound of the present invention is preferably administered orally or intravenously. The compound is preferably formulated prior to administration, the selection of which route to use will be made by the attending physician or qualified care giver. Most preferably, a composition of the compound of the present invention is formulated for oral administration. A particularly preferred dosage form of the compound of the present invention is a tablet, caplet or capsule. Also preferred is a rapid release solid formulation which may be appropriately coated or flavored to enhance ease of compliance with therapy depending on the patient's age or preferences. In yet another preferred embodiment, the pharmaceutical composition of the present invention further comprises one or more additional therapeutic agents.

Pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995). Thus, one of skill is able to formulate the compound of the present invention as a solid, liquid, intravenous, subcutaneous depot, transdermal patch or other formulation without undue experimentation.

The compound of the present invention is generally effective over a wide dosage range. For example, dosages per day may fall within the range of about 1 mg to about 1000 mg total daily doses, preferably 10 mg to 500 mg total daily dose. More preferably, the dosing is about 50 to 200 mg per day. Most preferably, the dosing is about 50-80 mg twice daily (b.i.d). In some instances doses below the lower limit of the aforesaid ranges may be more than adequate, while in other cases still larger doses may be employed. The above dose ranges are not intended to limit the scope of the invention in any way. It will be understood that the amount of the compound of the invention actually administered will be determined by a physician in view of the relevant circumstances including the condition to be treated, the chosen route of administration, the compounds administered in case of a cocktail or a fixed-dose combination therapy, the age, weight, response of the individual patient, and the severity of the patient's symptoms among other factors.

c-Met Relevant Tumors And Xenograft Models c-Met overexpression is a common feature for many human tumors, including lung, breast, colorectal, gastric, renal, pancreatic, head and neck (1,2). c-Met activating mutations in the kinase domain are implicated as the cause for several tumors, such as hereditary papillary renal cell carcinoma, childhood hepatocellular carcinoma, and gastric cancer (3-7). c-Met inhibitors from Pfizer demonstrated antitumor efficacy in many human xenograft tumors, including U87MG, GTL16, H441, Caki-1, and PC3 (8).

1. Christinsen, J G., Burrows, J., and Salgia, R. Cancer Letters 225: 1-26, 2005.
2. Birchmeier, C., Birchmeier, W., Gherardi, E., and Vande Woude, G F. Nat Rev Mol Cell Biol 4: 915-925, 2003.
3. Di Renzo, M F., Olivero, M., Martone, T. Et al. Oncogene 19: 1547-1555, 2000.
4. Lee, J H., Han, S U, Cho, H. et al. Oncogene 19: 4947-4953, 2000.
5. Ma, P C., Kijima, T., Maulik, G. et al. Cancer Res 63: 6272-6281, 2003.
6. Park, W S., Dong, S M., Kim, S Y. et al. Cancer Res 59: 307-310, 1999.
7. Schmidt, L., Duh, F M., Chen, F., et al. Nat Genet. 16: 68-73, 1997.
8. Zou, H Y., Li, Qiuhua., Lee, J H., et al. Cancer Res 67: 4408-4417, 2007.

I claim:
1. A compound of formula

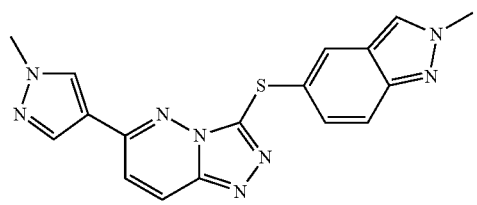

or a pharmaceutically acceptable salt thereof.

2. A salt according to claim 1 wherein the salt is the hydrochloric acid salt, bisulfate salt, or methanesulfonic acid salt.

3. A pharmaceutical composition comprising the compound of claim 1, or a pharmaceutically acceptable salt thereof and one or more pharmaceutically acceptable carriers or diluents.

4. A method of treating cancer selected from gastric, glioblastoma, and pancreatic cancer comprising administering a therapeutically effective amount of the compound or salt of claim 1, to a patient in need thereof, wherein treating is tumor growth arrest, inhibition of tumor growth, and/or reduction in severity or effect of cancer.

* * * * *